US005600311A

United States Patent [19]
Rice et al.

[11] Patent Number: 5,600,311
[45] Date of Patent: Feb. 4, 1997

[54] ENVIRONMENTAL CONTROL SYSTEM WITH AUXILIARY CONTROL INTERFACE

[75] Inventors: Richard F. Rice, Huntsville; David M. Kelly, Madison; Daryl L. Smith, Moulton, all of Ala.

[73] Assignee: Rice-Kelly Research & Engineering, Inc., Huntsville, Ala.

[21] Appl. No.: 422,881

[22] Filed: Apr. 17, 1995

[51] Int. Cl.⁶ .................................................. H02B 15/00
[52] U.S. Cl. ......................................... 340/825.19; 341/21
[58] Field of Search .......................... 340/825.19; 341/21; 379/52; 434/112

[56] References Cited

U.S. PATENT DOCUMENTS

| | | |
|---|---|---|
| 3,911,316 | 10/1975 | Feick et al. . |
| 4,697,231 | 9/1987 | Boytor et al. . |
| 4,859,995 | 8/1989 | Hansen et al. . |
| 4,979,094 | 12/1990 | Gemmell et al. . |
| 5,016,003 | 5/1991 | Rice et al. . |
| 5,126,731 | 6/1992 | Cromer, Jr. et al. . |
| 5,345,226 | 9/1994 | Rice et al. . |
| 5,365,026 | 11/1994 | Cromer, Jr. et al. ........... 340/825.19 X |

FOREIGN PATENT DOCUMENTS 2136617  9/1984  United Kingdom .

OTHER PUBLICATIONS

"Deuce Instruction Manual," DU–IT Control Systems Group, Inc., Shreve, Ohio, Apr. 1986.
"Operator's Manual For Hecs–1," Prentke Romich Company, Wooster, Ohio (undated).
"Changing Lives," Prentke Romich Company catalog, Wooster, Ohio, Aug. 1992.

Primary Examiner—Edwin C. Holloway, III
Attorney, Agent, or Firm—Nixon & Vanderhye P.C.

[57] ABSTRACT

An environmental control system for the severely disabled provides a "pass through" mode that allows a system output to mimic or emulate a user controlled switch input. The pass through mode permits a single user controlled switch to be shared among multiple systems for the disabled. In the normal mode, the user controlled switch controls various control functions provided by the environmental control system. In the "pass through" mode, the environmental control system operates "transparently" and passes the switch closures through to an electronically-controlled switch that appears electrically like a manually actuated switch to control other equipment for the disabled. The pass through mode is exited upon user actuation of the user controlled switch for more than a programmed time period and/or automatically upon occurrence of certain events (e.g., telephone ringing detection).

31 Claims, 8 Drawing Sheets

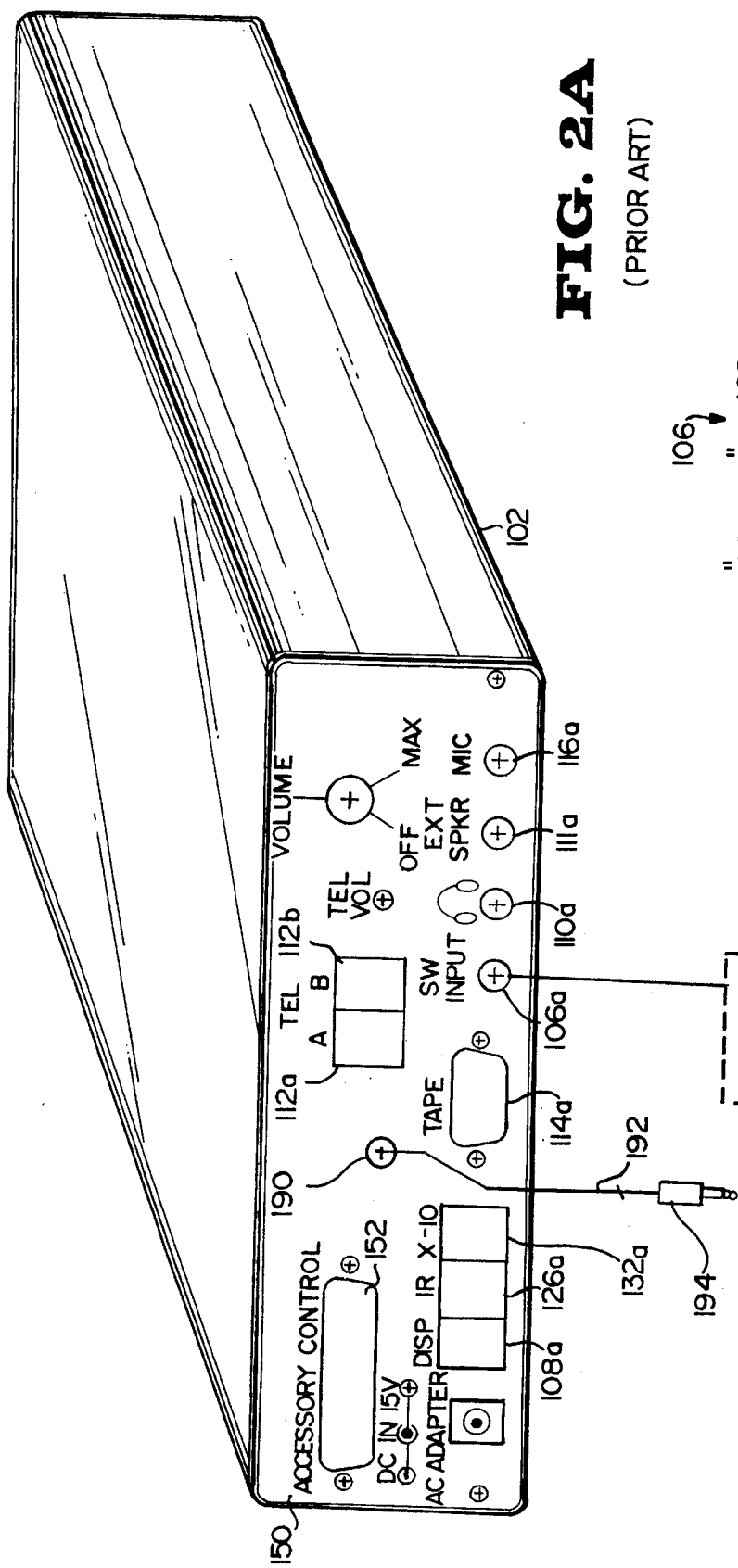
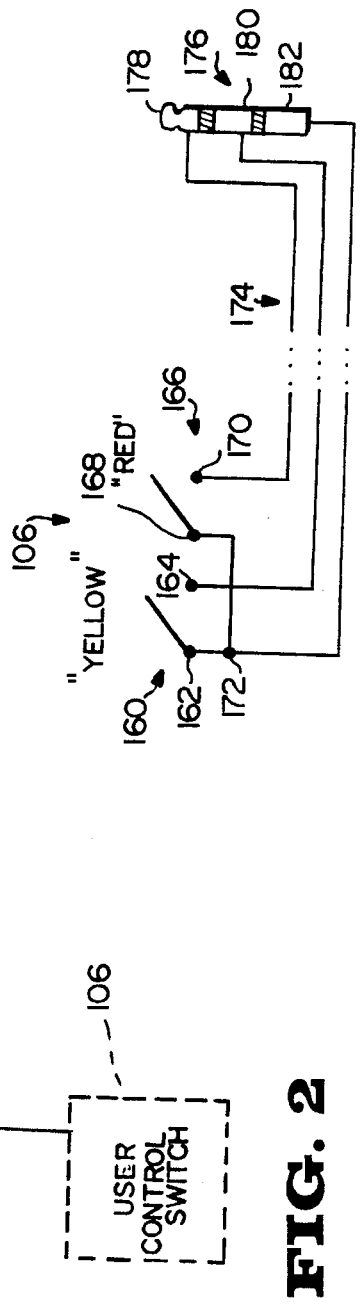
FIG. 2
FIG. 2A (PRIOR ART)

FIG. 4 EXTERNAL/AUX CONTROL INTERFACE

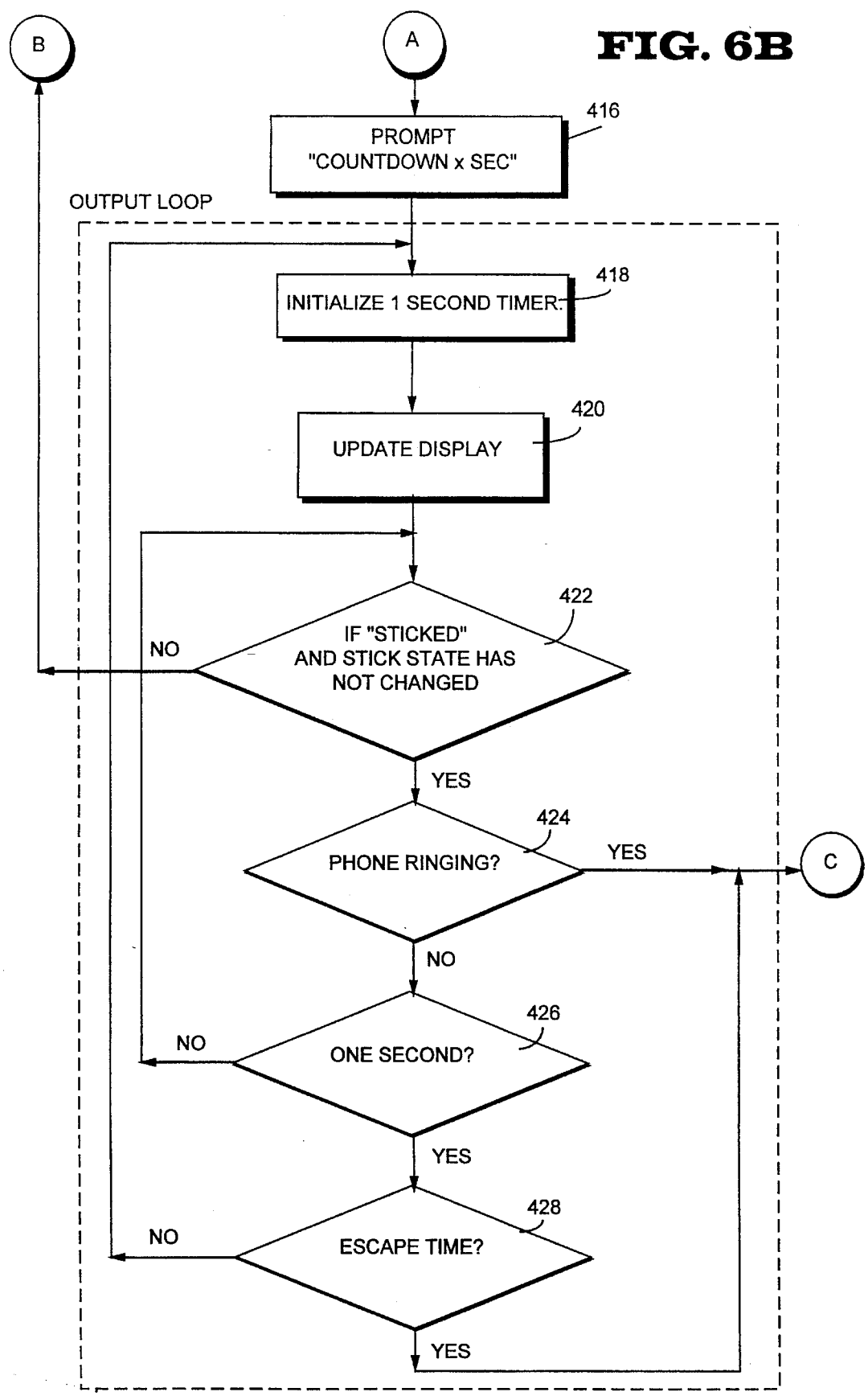

ENVIRONMENTAL CONTROL SYSTEM WITH AUXILIARY CONTROL INTERFACE

FIELD OF THE INVENTION

This invention relates to environmental control systems ("ECSs") for the physically challenged, and more particularly, to environmental control systems providing an auxiliary control interface for use as a user-controlled switching input to other control devices. Still more particularly, this invention relates to an environmental control system responsive to standard user control switch inputs that, in one mode, provides a switched output that emulates, under microprocessor control, the user control switch inputs to control another ECS or other device.

BACKGROUND AND SUMMARY OF THE INVENTION

FIG. 1 shows an example of an environmental control system 100 generally of the type described, for example, in U.S. Pat. Nos. 5,016,003 and 5,345,226. System 100 is a versatile, responsive switch-activated environmental control system that allows users to control their environment, for example, turning on lights and appliances, changing television stations, adjusting volume levels, using a telephone, recording messages, calling a nurse or attendant, or controlling a hospital bed. For example, system 100 may include a main unit 102 that preferably is microprocessor-based and software-controlled. Main unit 102 interfaces with a user 104 through a user control switch 106 and a back lit display 108. In addition, main unit 102 may include a speech synthesizer that allows the system 100 to talk to user 104 through headphones 110, speakers, etc. User control switch 106 may be a conventional type of "dual action" switch normally controlled by a severely disabled person, e.g., a two-position switch such as a "sip and puff" switch, a tongue switch, a rocker switch, or a dual head switch activated by slight left/right head motion. Such switches often provide a single-pole-double-throw (SPDT) set of switch contacts (this same switching action can also be effected by a pair of normally open SPST switches) for three distinct, mutually-exclusive switch positions (e.g., contact set one closed, contact set two closed, or both contact sets open) corresponding to the physical state of a user relay-controlled actuator (e.g., "sip," "puff," and not activated). See FIG. 2A. Many severely disabled individuals cannot control a more complex switch or user control interface such as those found on typical home appliances and equipment. Therefore, all user control operations and functions performed by system 100 are capable of being actuated and controlled using only such a 3-state "dual action" user control switch 106.

In the system 100 shown in FIG. 1, a user-friendly "menu-driven" menu structure provides control in response to the user control switch 106. Display 108 may display a sequence of menu options to the user 104, and a speech synthesizer internal to main unit 102 may generate corresponding audible menu prompts to guide the user. The menu prompts may be nested to whatever level is desired. Such displayed and/or audible menus allow user 104 to access an almost unlimited variety of different control functions using only a dual action user control switch 106.

For example, the user may control telephone electronics internal to main unit 102 and connected to a telephone line/jack 112. The user may optionally control a tape recorder 114 to dictate, play back or both. The user 104 may speak into a user microphone 116 to interface with the telephone electronics and/or tape recorder 114, and can hear telephone and tape recorder audio through speaker 111 and/or headphones 110 and/or internal speaker within 102. User 104 may also, through main unit 102 and its menu-driven user interface, actuate conventional home entertainment appliances such as a television set 118, a compact disc player 120, a stereo receiver 122, and/or a video cassette recorder 124 via an infrared (IR) remote control link 126 driven by main unit 102. User 104 may also control 110 VAC operated electric appliances (e.g., a lamp 128, a fan 130, etc.) via a conventional X-10 power line interface 132 which may inject signals into house wiring to control remotely located/operated conventional X-10 switching modules 134A, 134B. User 104 may also actuate relay-controlled switch contacts within main unit 102 to interface with other systems and appliances such as, for example, hospital lights 136, a nurse call button 138, controls of an electrically-operated hospital bed 140, etc.

The array of control interfaces provided by main unit 102 is very flexible for control of a wide variety of equipment and appliances. Moreover, despite such versatility of environmental control system 100, further improvements are possible.

In particular, severely disabled users 104 may, in some cases, want to control more than just one system designed to interface and be operated by a dual action user control switch 106. For example, some users may wish to control an environmental control system 100 such as is shown in FIG. 1, and also control an additional system such as, for example, "augmentative communication device" ("ACD"). An ACD permits a non-verbal user, through switch control, to invent/construct phrases and sentences and then communicate them either via printed page or via voice synthesizer. A severely disabled person normally controls an ACD using a dual action user control switch. In many instances, however, it is impractical or impossible for a user to use, operate, or reach more than a single user control switch 106.

For example, users with limited head motion may be unable to select between the straw end of two different "sip and puff" switches. In the case of a tongue switch, it is most times impossible for a user to operate a pair of co-located dual action switches. Rocker switches are often used by people who have control of one (and only one) hand or finger; it may be impossible for such users to reach, much less control, more than one rocker switch. Severely disabled users cannot operate more than one pair of minimum deflection head switches since they typically lack head control to move their head or other extremity in more than one unique back-and-forth trajectory.

Even if a particular disabled user could operate more than one user control switch 106, there are disadvantages to providing or requiring a second user control switch. For example, a second switch may be too expensive. A good quality sip and puff switch, including extension cable, adaptor (if required), mechanical mounting hardware and custom installation, could cost in excess of $300.00 at today's prices. Another "expense," which may be more serious than simply monetary, is the space cost for placement of a second switch. If a severely disabled person is using a respirator and an environmental control system 100 and display 108 mounted on a gooseneck, there usually is no space to mount another switch. In fact, the user's immediate area is typically 100% utilized and frequently gets disturbed due to need for fast accessibility by personal care attendants, family members and nurses in administering oral medicine, giving IV medication, and performing personal care activities. A second user control switch for a severely disabled individual requiring this level of care is usually impractical to consider.

In the past, users sometimes solve the problem of trying to operate two different systems with the same user control switch 106 by having an attendant unplug the switch from one unit and plug it into the other unit as required. For example, a severely disabled person might have an attendant disconnect the user control switch 106 from environmental control system main unit 102 and connect it instead to an ACD when the user wants to communicate using the ACD. Later, when the user finishes a particular communications task using the ACD, the user may then ask the attendant to disconnect the ACD and reconnect the environmental control system 100 so the user can control their environment. This manual plugging and unplugging of a user control switch is highly inconvenient, however, since the user may require the capabilities of both types of equipment simultaneously. What the severely disabled user really wants is to be as independent as possible and therefore in "real time," decide for himself/herself which system functions to control.

The present invention provides a solution to this problem. In accordance with one aspect of the present invention, an environmental control system 100 is improved to include an auxiliary control interface. The auxiliary control interface, which may be operated under control of a microprocessor responsive to the user control switch 106, appears electrically, from the "viewpoint" of a further controlled system or device connected to the auxiliary control interface, to be electrically the "same" or "equivalent" to the manually-actuated contacts of user control switch 106. When the user wants to operate the auxiliary control interface, he/she operates the user control switch 106 in accordance with special menu-driven selections, to place environmental control system 100 into a special "pass through" mode. When operating in this special mode, the environmental control system 100 responds to closures of user control switch 106 by closing electronically controlled switching circuits that electrically "look like" user control switch 106. Main unit 102 detects the switch closures provided by the user through user control switch 106, and responds to those switch closures by, for example, electrically operating a pair of SPST relays so that the relay switch closures "mimic" or "emulate" the switch closures provided by user control switch 106. In this way, the auxiliary control interface interfaces to another existing disability system or device by emulating the electrical switching action of a conventional, mechanically-actuated user control switch 106 operated by the user. For example, the auxiliary control interface may provide the electrical and functional equivalent of a "sip" and "puff" switch interface to an existing appliance in response to microprocessor control based on user actuated "sip" and "puff" switch inputs.

In accordance with another aspect of the present invention, the mimicry or "emulation" provided by the auxiliary control interface is intentionally made imperfect to provide a means by which the user may control the environmental control system 100 to cease operating in the special "pass through" mode. Generally, the user has only the user control switch 106 by which he must control all aspects of the operation of the environmental control system 100 and any other system or device attached to and controlled by the auxiliary control interface. In accordance with this further aspect provided by the present invention, once the environmental control system 100 is operating within the special "pass through" mode, it continually monitors certain user input switching characteristics to determine whether it should cease operating in the "pass through" mode and begin operating in "normal" mode to permit the user to control devices in his environment such as TV 118, tape recorder 114, etc. For example, the main unit 102 may time how long the user provides a manually actuated closure of user control switch 106 whenever environmental control system 100 is operating in the "pass through" mode. If the amount of time matches certain preset time parameters (e.g., longer than a certain amount of time), main unit 102 may sense this and cause system 100 to cease operating in the "pass through" mode and to instead begin operating in the "normal" mode.

In accordance with another aspect provided by the present invention, environmental control system 100 may optionally immediately switch from the special "pass through" mode to the "normal" mode upon the occurrence of some event other than user actuation of switch 106 (e.g., detecting that the telephone has begun ringing) to allow the user the convenience of automatically changing back to a "normal" mode of operation (e.g., to permit the user to conveniently answer the telephone without manually telling the system 100 to cease operating in the "pass through" mode).

BRIEF DESCRIPTION OF THE DRAWINGS

These and other features and advantages provided by the present invention will be better and more completely understood by referring to the following detailed description of a presently preferred exemplary embodiment in conjunction with the drawings, of which:

FIG. 2 shows an example of an environmental control system main unit provided in accordance with the preferred embodiment of this invention;

FIG. 2A shows a schematic diagram of a (prior art) user control switch 106;

FIGS. 6A–6C together are a flowchart of an example of program control steps that may be performed by the FIG. 3 microprocessor.

DETAILED DESCRIPTION OF A PRESENTLY PREFERRED EXEMPLARY EMBODIMENT

Figure 1:
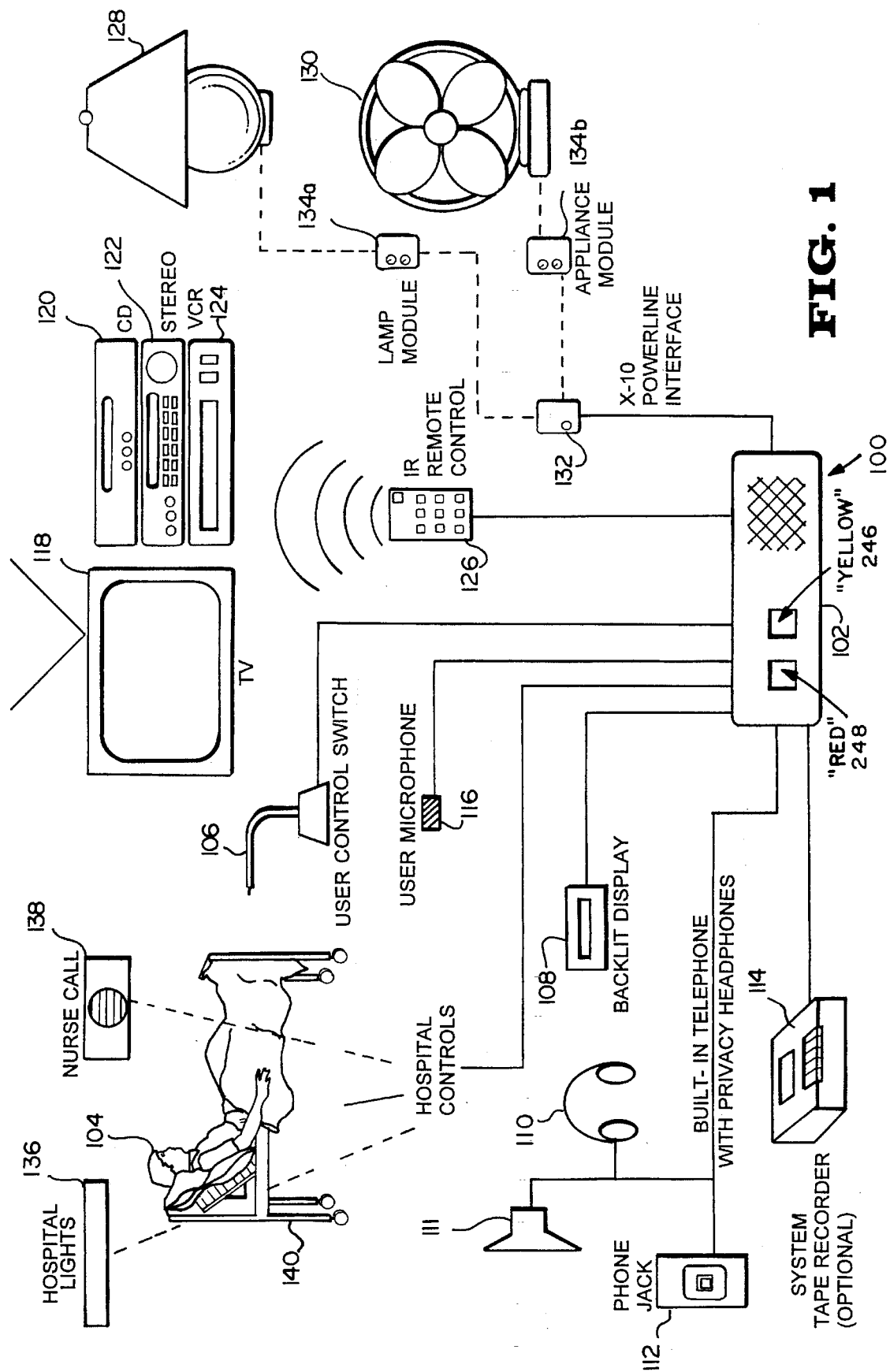
FIG. 1 is a schematic illustration of an example of an environmental control system with which the preferred embodiment of the present invention may be advantageously used.

FIG. 2 shows an environmental control system main unit 102. A rear panel 150 includes various connectors for attachment to the equipment and devices shown in FIG. 1. For example, a microphone jack 116A establishes electrical connection with a user microphone 116, and a headphone jack 110A establishes electrical connection with headphones 110. An external speaker jack 111A similarly may receive a plug to an external speaker 111. Telephone jacks 112A, 112B may be used to connect main unit 102 to telephone line(s)

112. A connector 108A may connect main unit 102 to display 108, a connector 126A may connect the main unit to IR remote control 126, and a connector 132A may connect the main unit to the X-10 power line interface 132. Similarly, a connector 114A may connect the main unit 102 to a tape recorder 114. The main unit rear panel 150 may also include an "accessory control" connector 152 for connecting main unit 102 to various devices and systems such as hospital lights 136, nurse call station 138, etc.

In addition, user control switch 106 connects to main unit 102 by plugging into a switch input jack 106A provided on rear panel 150. Switch 106 generally is located a few feet from main unit 102, and connects to the main unit via a three-conductor cable 174 terminating in a conventional ⅛-inch "stereo" plug 176.

In the preferred embodiment, rear panel 150 also includes a jack 190 that provides an auxiliary control interface with other disability equipment designed to be controlled by a conventional single or dual user-actuated user control switch 106. Such other disability equipment might be, for example, an ACD or other communications, speech synthesis or writing tool; another environmental control system; an interface to a personal computer; an electric wheelchair control; or any other device designed to be actuated by a user control switch 106. In the preferred embodiment, jack 190 may be connected to such other device via a cable assembly 192 terminating in a standard ⅛-inch three-conductor "stereo" plug 194 at each end. Plugs 194 may be identical to the plug 176 that is used to connect conventional user control switch 106 to main unit rear panel jack 106A.

Main unit 102 in a preferred embodiment operates in two different modes. In one mode, which may called the "normal" mode, user actuation of user control switch 106 controls the various devices connected to the main unit but has no effect on jack 190 (and thus also plug 194 that connects to another device). In another "pass through" mode of operation, main unit 102 "transparently" passes user control switch 106 actuations through to plug 194 so that, to other disability equipment connected to the plug, it "appears" as if user control switch 106 is directly connected to the other device rather than being connected through main unit 102. Thus, in this "special" mode of operation, plug 194 connected to main unit 102 looks and acts as if it were connected directly to user control switch 106. Main unit 102 may provide additional control features to selectively switch between the "normal" and "pass through" modes.

FIG. 2A is a detailed electrical schematic diagram of a conventional user control switch 106. User control switch 106 includes a first SPST switch 160 (having a first contact 162 and a second contact 164), and a second SPST switch 166 (having a first contact 168 and a second contact 170). Such conventional user control switches 106 typically connect one of the contacts of each of the switch contact sets 160, 166 in common. Thus, in the example shown, contact 162 of switch contact set 160 is electrically connected to contact 168 of switch contact set 166 at an electrical connection 172. In the preferred embodiment, each of switch contact sets 160, 166 is normally open (i.e., there is no electrical contact between switch contacts 162, 164 or between switch contacts 168, 170), whenever the user is not manually actively actuating a switch. This "normally open" arrangement is conventionally accomplished by spring-loading or other conventional mechanical biasing techniques as is commonly found in any standard dual contact switch or pair of SPST momentary switches, such as, for example, a "dual rocking lever" general purpose dual switch, a tongue switch, an air cushion switch, a pneumatic "sip-puff" switch, etc. Sometimes, the mechanical actuating mechanism (not shown) for user control switch 106 permits only one of switch contact sets 160, 166 to be closed at one time. For example, with a conventional "sip" and "puff" switch, the user can either "sip" (inhale through a straw), or "puff" (exhale into the straw) but cannot sip and puff simultaneously. In this example, a "sip" might cause switch contact set 160 to close, thereby establishing electrical contact between switch contacts 162, 164. When the user "puffs," the other switch contact set 166 may close, establishing electrical contact between switch contacts 168, 170. Of course, a "sip and puff" switch may be wired so that "sipping" causes contact set 166 to close and "puffing" causes contact set 160 to close. In this particular example of a "sip and puff" user control switch 160, switch contact sets 160 and 166 never close simultaneously but instead are actuated on a mutually exclusive basis, but other types of suitable user control switches permit both closures simultaneously.

Switch contact sets 160, 166 are connected to a conventional ⅛-inch "stereo" three-conductor electrical plug 176 through a 3-conductor cable 174. Plug 176 has three electrical contacting portions "tip" 178, "ring" 180, and "sleeve" 182. Plug 176 dimensioned to mate with corresponding jack 106A mounted on the main unit rear panel 150.

Figure 3:
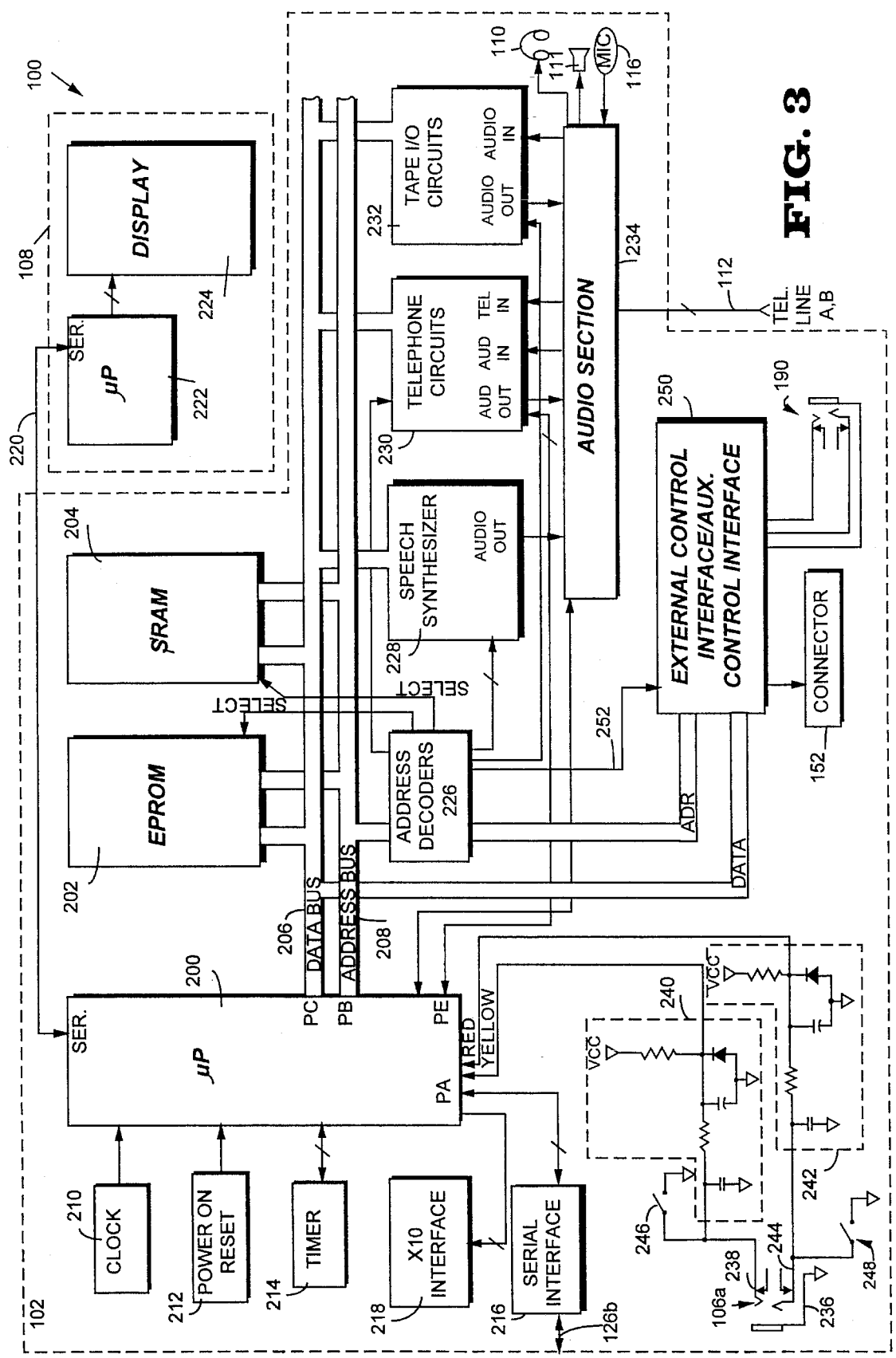
FIG. 3 shows a schematic block diagram of another, more detailed example of a preferred embodiment environmental control system provided in accordance with the present invention.

FIG. 3 is a block diagram of another example showing a detailed internal electrical architecture of a system 100. Main unit 102 in the preferred embodiment includes a microprocessor 200 that performs steps under control of a program stored in an EPROM or other non-volatile memory 202. Microprocessor 200 accesses EPROM 202 (and may also access other memory devices such as a RAM 204) via a data bus 206 and an address bus 208.

Microprocessor 200 is supported by a conventional clock oscillator 210, a power-on reset circuit 212, and an internal timer 214. Timer 214 may, for example, comprise a conventional timer chip that allows microprocessor 202 to load a value representing a predetermined time interval and to be informed (e.g., by an interrupt or otherwise) when the time interval has elapsed (as will be understood by those skilled in this art, the functions of hardware timer 214 could be performed by microprocessor 200 under software control if desired). For example, a Motorola 68HC11 provides several internal timers. There are hardware timers associated with the input ports to which switch contacts 160, 166 connect in the preferred embodiment. On switch closure, the appropriate timer is set, and if it goes off and the switch has not opened then the input is considered to be valid (and debounced). Similar timers may be associated with output ports used to generate the X-10 protocol. An internal timer may count clock (210) cycles. On overflow, an interrupt occurs. These overflows may be counted and combined with the clock counter to provide a resolution of 500 ns over a 35 minute period. For all other events, the preferred embodiment uses a periodic interrupt often called a "real time interrupt" or RTI. This interrupt is set to trip 61 times per second. If the global variable "tick" is non-zero, "ticks" contents are decremented during the service of this interrupt. Most time intervals can be measured in "ticks."

Microprocessor 200 also communicates with (or has integrated within it) a serial interface 216 (e.g., to provide data to IR remote control 126). Microprocessor 200 has a serial communications path 220 to communicate with a display microprocessor 222 within display unit 108 (path 220 may be driven by serial interface 216, with a MUX multiplexing the interface between IR interface 126b and path 220). In the preferred embodiment, display microprocessor 222 includes its own software to control how information is displayed on an conventional back lit LCD display 224.

Microprocessor 200 also communicates via data bus 206 and address bus 208 (always via address decoders 226) with a speech synthesizer 228, telephone circuits 230, and tape I/O circuits 232. Tape I/O circuits 232 are connected to tape recorder 114, and telephone circuits 230 are connected to telephone line(s) 112. Audio to/from speech synthesizer 228, telephone circuits 230 and tape I/O circuits 230 are routed, amplified and mixed by audio section 234. Audio section 234 receives and amplifies input from microphone 116 to provide to telephone circuits 230 and tape I/O circuits 232, and amplifies audio received from these components and speech synthesizer 228 for reproduction by headset 110 and/or loudspeaker 111.

Microprocessor 200 receives, as inputs, the electrical connections from switch input jack 106A connected to user control switch 106. The "common" connection 236 of jack 106A (which is connected to the "sleeve" portion of plug 176 shown in FIG. 2A when that plug is plugged into the jack) is, in the preferred embodiment, connected to common potential. A further connection 238 of jack 106A (which in the preferred embodiment may connect to plug 176 "ring" conductor 180, for example), is connected to a microprocessor input port through a "debounce" circuit 240. This may be referred to as the "yellow" or "yellow stick" connection. Conventional debounce circuit 240 may be a low pass filter with a pull up resistor sourcing the current. The same pull up resistor in series with another resistor serve to limit current that will flow through the switch when closed. Debounce circuit 240 "debounces" and "pulls up" this "yellow" input to the microprocessor 200 so that the input is at logic level 1 ("high") whenever switch contact set 160 is open, and is at logic level 0 ("low") when the switch contact set 160 has been manually actuated by the user so that it is closed. A similar debounce circuit 242 is used to debounce and "pull up" the jack 106A connection 244 (which in the preferred embodiment is connected to plug 176 "tip" conductor 178—and thus to switch 166 contact 170). This debounced connection 244 provides a "red" or "red stick" input of logic level 1 ("high") when the user is not activating user switch contact set 166, and this "red" input falls to logic level 0 ("low") when the user manually actuates switch contacts 166 to close them. The "red" input is connected to another microprocessor input port different from the one the "yellow" input is connected to in the preferred embodiment.

In the preferred embodiment, a redundant "red" switch 248 mounted on main unit front panel 102 may be connected in parallel with user switch contact set 166, and a redundant "yellow" switch 246 mounted on the main unit front panel may be connected in parallel with user switch contact 160. This enables manual control inputs to be provided from a front panel of main unit 102, if desired. "Red" and "yellow" switches 246, 248 are named after the color of the front panel LED which lights in the preferred embodiment when the corresponding switch is closed. The LEDs are illuminated at the direction of software on microprocessor 200 after debounce. The base unit 102 may drive its LEDs with 8 bit latches exactly the same way as relays are driven. The display uses inverter logic gates as LED drivers attached to CPU output ports because the CPU ports can not source or sink enough current to light the LEDs in the preferred embodiment.

Figure 4:
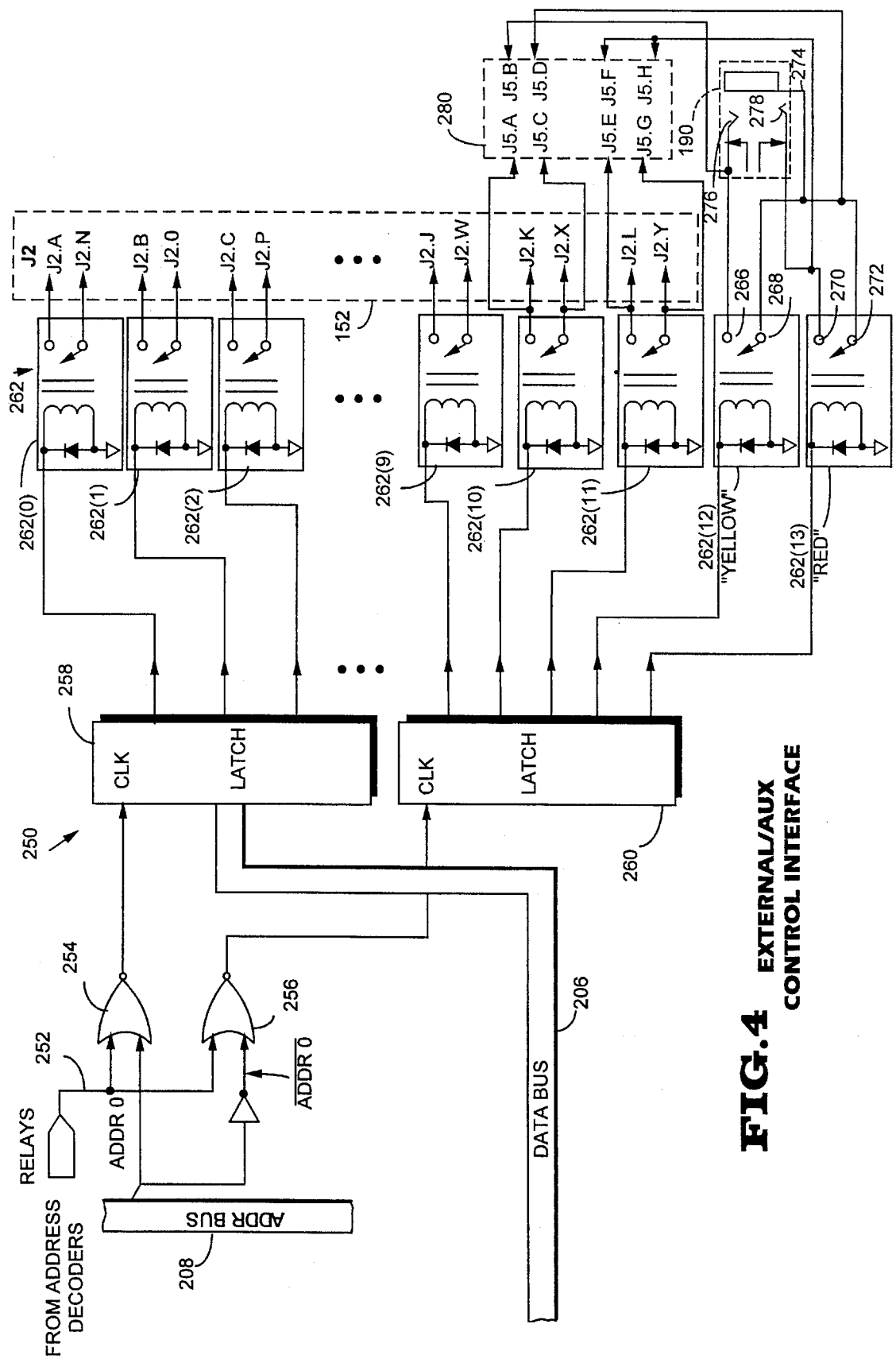
FIG. 4 shows a detailed schematic illustration of an example of one suitable arrangement of an external and auxiliary control interface that can be used in the FIG. 3 system.

In the preferred embodiment, microprocessor 200 is also connected (via data bus 206, address bus 208 and address decoders 226) to an external control interface/auxiliary control interface 250. This interface 250 contains electrically-actuated switches that allow microprocessor 200 to directly control switched outputs of accessory control connector 152 and jack 190. FIG. 4 is a schematic diagram of an example of a external control interface/auxiliary control interface 250 provided by the preferred embodiment in accordance with the invention.

Referring to FIG. 4, microprocessor address bus 208 and the "relays" output 252 of address decoders 226 are further decoded by NOR gates 254, 256 followed by inverters to provide OR logic (this logic can be considered part of the address decoder 226) providing clock input signals for a pair of 8-bit latches 258, 260. The microprocessor data bus 206 is written to the parallel data inputs of each of these latches 258, 260. In a preferred embodiment, the eight most significant bits of the address provided by microprocessor 200 onto address bus 208 selects the external control interface/auxiliary control interface 250 (by action of address decoders 226 and its output 252), with the least significant "ADDR0" bit of the address selecting between latch 258 and latch 260. In the preferred embodiment, address lines A8 through A15 plus the CPU's E clock are inputs to decoder 226. Eight address ranges of 256 bytes each are decoded by decoder 226. Devices connected to decoder 226 need only watch address lines A0 through A7 and their select line. Specifically the Real Time Clock (not shown) decodes A0 through A6 internally, ignoring A7. A0 may be decoded for additional latch selects.

Thus, microprocessor 200 can directly address each of latches 258, 260 on a "write only" basis. To write into latch 258, microprocessor 200 simply asserts the corresponding address on address bus 208 and asserts the desired data to be written into the latch on data bus 206. Similarly, to write to latch 260, microprocessor 200 asserts a different corresponding address on the address bus 208 and, similarly, provides the desired data to be written into the latch onto data bus 206.

In the preferred embodiment, the data stored within latches 258, 260 control the states of a bank of relay controlled switches 262. In the preferred embodiment, there is a one-to-one correspondence between SPDT relays 262(0)–262(13) and corresponding data bits of latches 258, 260. To open a corresponding relay switch 262, microprocessor writes a "zero" data bit into the appropriate corresponding bit position of latch 258, 260—and similarly, to close the corresponding relay contact the microprocessor writes a "one" into the corresponding latch data bit position. The relay-controlled switch contacts 266, 268 of relay switches 262 are connected to pins of auxiliary connector 152 to provide external access to the switched contacts for use in controlling external devices.

In the preferred embodiment, latch 260 has, in addition to "standard" auxiliary control relay outputs, two additional outputs ("YEL" and "RED") associated with auxiliary control interface jack 190. These additional outputs drive relays 262(12) and 262(13). The relay controlled switch contacts of these relays are connected across contacts of jack 190. In particular, one switch contact (268, 272) of each of relay controlled switches 262(12) and 262(13) is connected to a "common" contact 274 of jack 190. The other contact 266 of relay switch 262(12) is connected to a further contact 276 of jack 190; and similarly, the other contact 270 of relay switch 262(13) is connected to a further jack contact 278.

When microprocessor 200 writes a "zero" into the bit of latch 260 corresponding to the latch "YEL" output, the coil of relay 262(12) remains de-energized, the relay contacts remain open, and there is no electrical contact between jack 190 "common" contact 274 and the jack's contact 276. However, when microprocessor 200 writes a "one" to this latch "YEL" data bit, the coil of relay 262(12) is energized, causing its contents to close and establish an electrical contact between jack 190 contacts 274 and 276. Microprocessor 200 can similarly control whether there is or is not electrical contact between jack 190 contacts 274, 278 by selectively writing a logical level "one" or "zero" to latch 260 data bit "RED" to thereby control whether relay 262(13) is open or closed.

In the preferred embodiment, a further electrical connector 280 may be provided in parallel with the three electrical contacts of jack 274, 276, 278 (as well as other relay contacts such as, for example, those provided by relays 262(10) and 262(11)).

Figure 5:
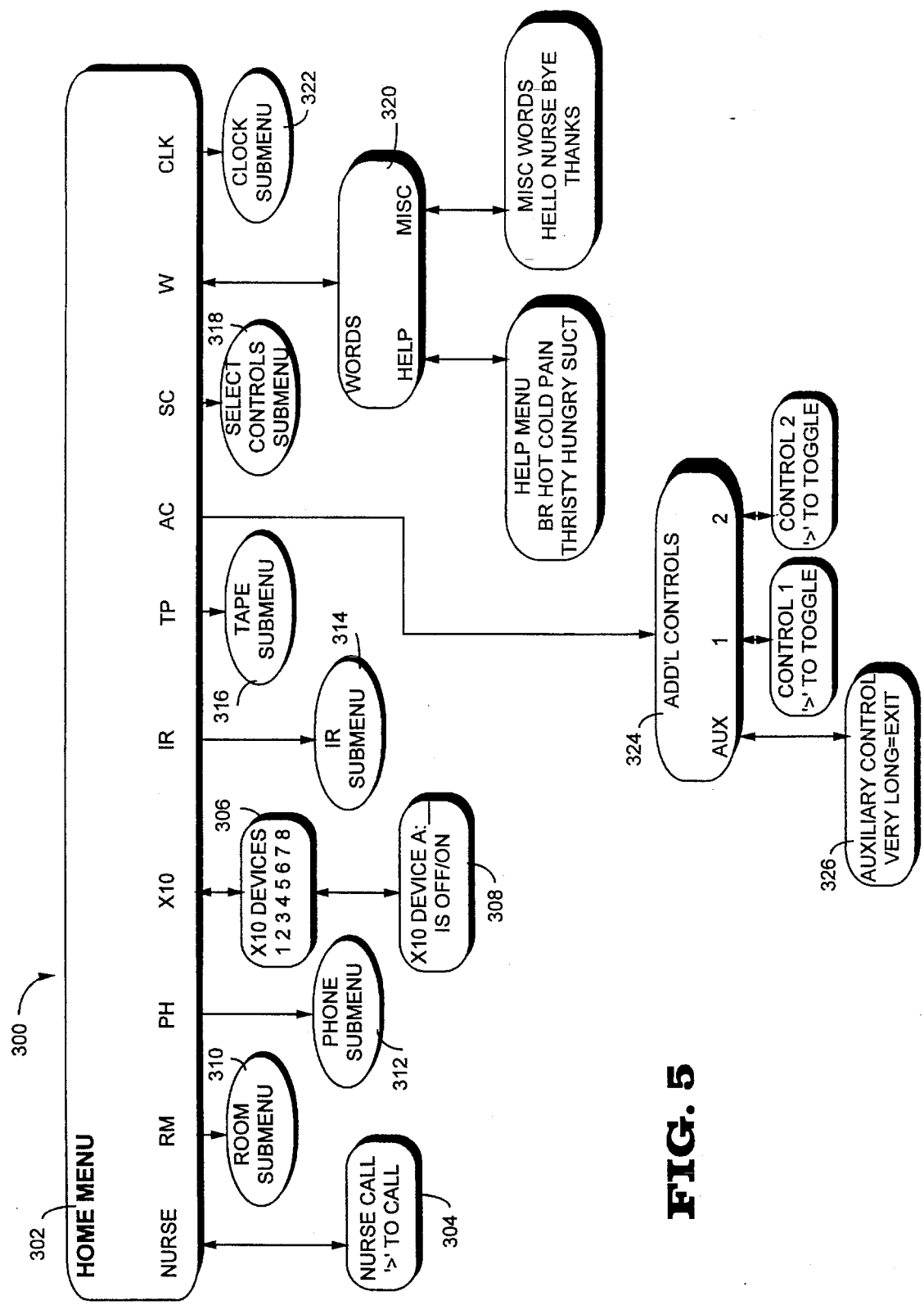
FIG. 5 shows an example of a user interface menu structure that may be provided by the system shown in FIG. 3.

FIGS. 5 and 6A–6C illustrate how the preferred embodiment microprocessor 200 controls the closure of relays 262(12), 262(13) under program control. FIG. 5 is a diagram of an example of an hierarchical user (menu) interface. This interface 300 includes a "home" menu 302 that allows the user to select various control options through actuation of the user control switch 106. In general, not actuating user control switch 106 causes no action to occur; actuating one of the two switch closures provided by the user control switch (e.g., "yellow") effects a control action; and providing an alternate and/or additional actuation of the user control switch (e.g., "red" closure) causes an "escape" to return to a previous menu level. As a specific example, sip and/or puff action on a pneumatic straw-type user control switch 106 causes two independent, mutually exclusive electrical closures to be made. The dwell time for each switch closure is a direct function of the length of time each sip/puff is held by the user, via sipping and puffing on their "straw switch," operates system 100 via user menus and acoustic feedback. Scanning options may be displayed on a display 108, and sounded through a loudspeaker 111, headphones 110, or speaker internal to 102 in a natural human voice in synchronism with the scan. The scan provides opportunities to select control over different appliances and devices in a preassigned order. From the home menu, a momentary "yellow" switch action starts the menu scan. A subsequent switch action after a desired function is presented audibly and/or visually on 108, yet before the next function is presented, will select that function. Further "yellow" switch actions further define the choice of action the user desires. "Red" switch actions typically "back up" to the prior level of definition. See U.S. Pat. No. 5,016,003, which also explains that in certain specific control functions, different types of closures may mean different things.

Thus, for example, to select "nurse call" from the "home" menu, the user may control system 100 to start "scanning" the menu options in sequence and again actuate the user control switch 106 after speech synthesizer 228 utters (and/ or display 108 displays) the "nurse" prompt. This actuation instructs main unit 102 to enter the "Nurse Call" menu. Further actuation of the "yellow" switch activates relay 262(11) presenting the appropriate signal on 152 to perform the nurse call function. Similarly, to selectively actuate and deactuate appliances 128, 130 controlled by X-10 power line interface 132, the user may actuate the user control switch 106 to start main unit 102 scanning the home menu options 302, and provide an appropriate switch closure upon hearing/seeing the "X-10" prompt to access to "X-10 device's" submenu 306. Scanning this X-10 device's submenu 306, in turn, may provide prompts for each of the various connected X-10 controlled devices. Further actuating the user control switch 106 upon seeing/hearing the appropriate prompt allows the user to toggle X-10 control of appliances such as fan 130 and lamp 128 on and off. The X-10 does not specifically activate relays the way nurse call does in the preferred embodiment. Thus, user selection on the input switches 106 does not always directly correspond to direct hardware (relay) output. Sometimes the user only selects a menu. Sometimes the user starts a complex series of actions which produce a simple result. For example, selecting the final stage in the X-10 menus causes 102 to send a precisely timed serial data stream through the X-10 interface which is coupled to the power lines and makes its way to an actual X-10 module which performs the task.

The user providing switch closures in response to other "home" prompts allows the user to control hospital television and bed controls by accessing a "room" submenu 310, control the telephone circuits 230 (via "phone" submenu 312), control the IR remote control 126 (via the "IR submenu" 314), control tape recorder 114 (via the "tape" submenu 316), set various parameters such as audio output sound levels (via a "select controls" submenu 318), control the speech synthesizer 228 to utter certain words (via a "words" submenu 320), and receive current time of day and date (via a "clock" submenu 322).

In addition, the preferred embodiment provides an "additional controls" submenu 324 that allows the user to control accessories connected to connector 152, and to also activate the auxiliary control interface. In the preferred embodiment, when the main unit 102 scans to the "AC" ("accessory") option on the "home" menu 302, the user may provide a "yellow" switch actuation of user control switch 106 to begin scanning the functions provided by "additional controls" submenu 324. These submenu functions allow use of an additional switch-controlled device and control of external devices connected during system installation and set up. During a configuration process (that may also be menu driven), system 100 can be "configured" to add or delete control options within submenu 324. To activate the auxiliary control interface provided by the preferred embodiment, the user may select the "AUX" option from submenu 324 by providing an appropriate actuation of user control switch 106 when the corresponding menu prompt is presented. A further "yellow" actuation of user control switch 106 controls system 100 to begin using another disability equipment connected to the jack. This action puts the main unit 102 into a "pass through" mode, allowing the user's dual contact user control switch 106 to control the other disability equipment. To return to control of the main unit 102 in the preferred embodiment, the user may provide any actuation of user control switch 106 for more than a programmed time period (e.g., 7 seconds). In the preferred embodiment, main unit 102 displays a countdown on display 108 whenever the user control switch 106 is actuated during this "pass through" mode. If the countdown display reaches zero (indicating that the user has actuated the user control switch 106 continuously for the programmed duration), main unit 102 disables the "auxiliary control" operation and returns to the "accessory" submenu of home menu 302.

Figure 6A:
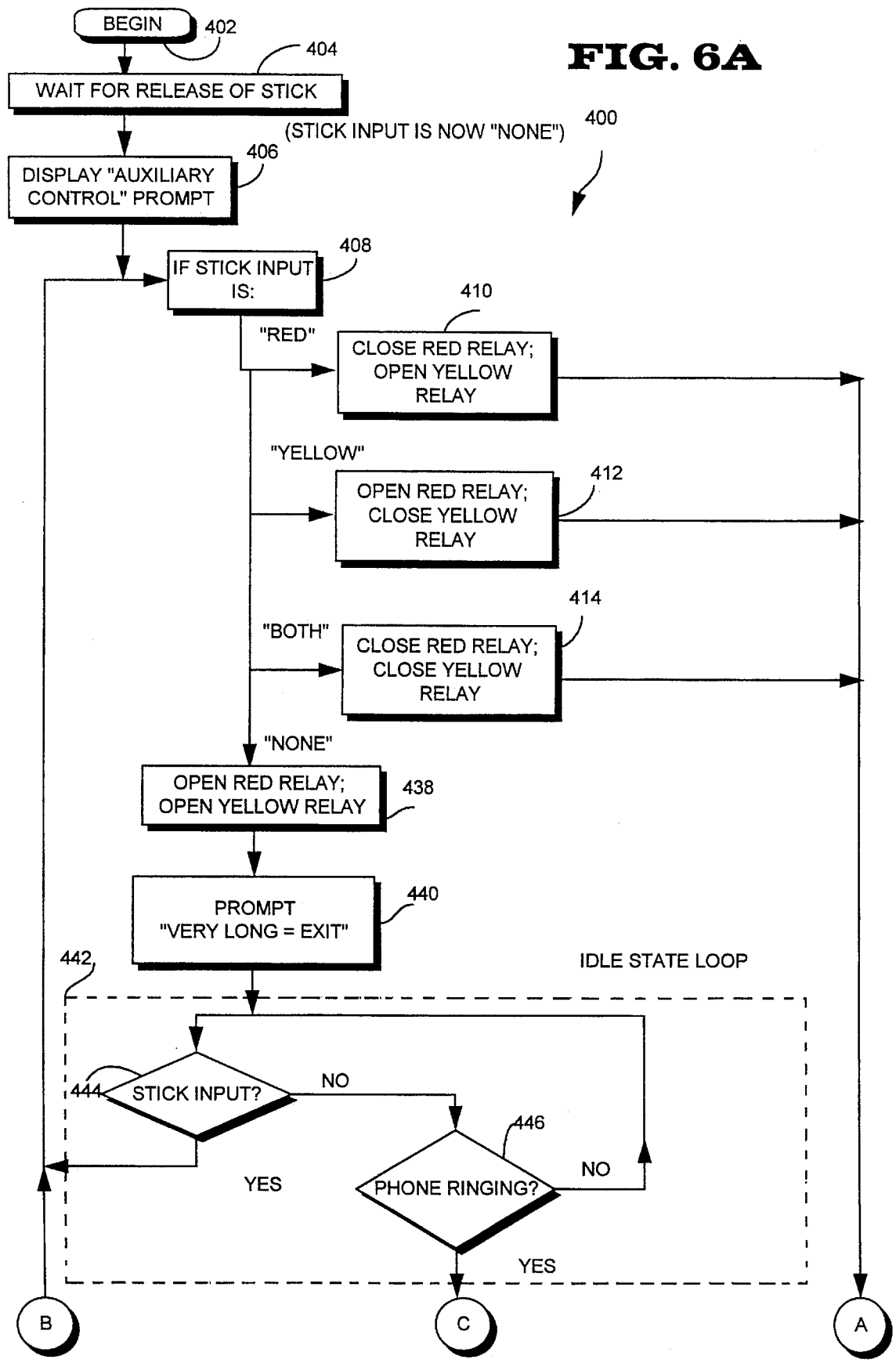
Figure 6C:
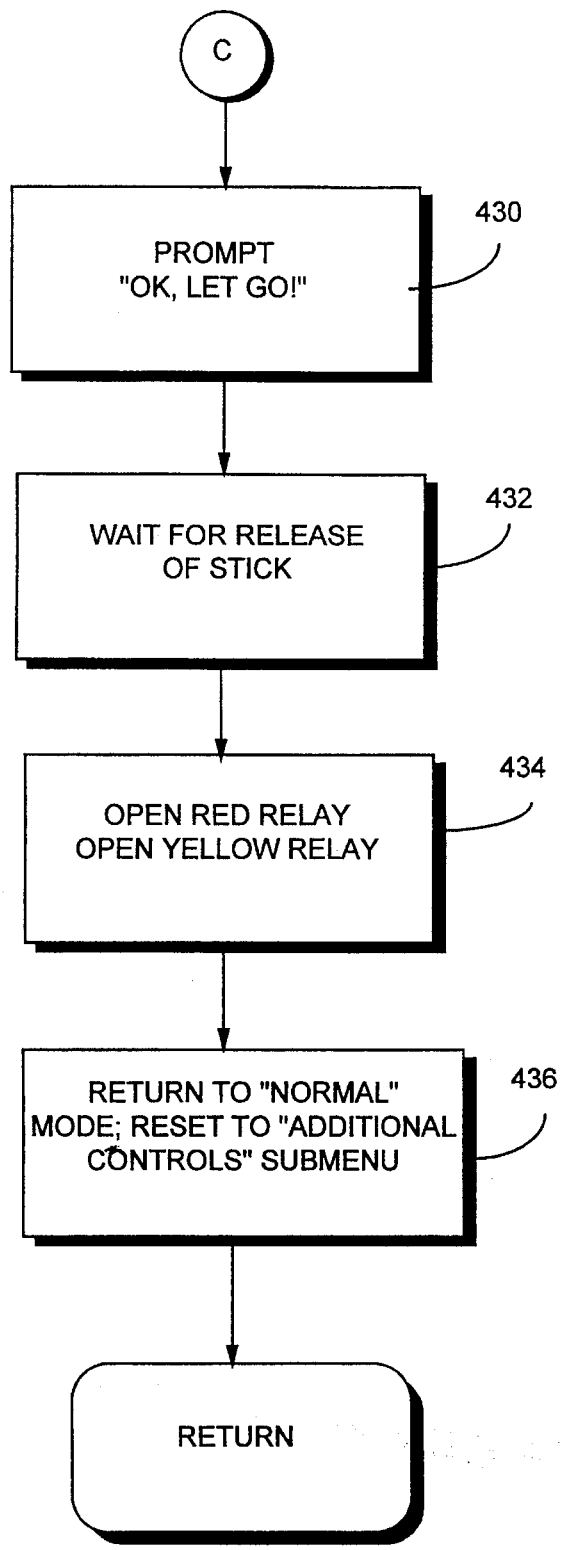

FIGS. 6A–6C are a flowchart of an example of program control steps performed by microprocessor 200 to provide the "auxiliary control interface" described above. If the user selects the "AUX" option from the "additional controls" submenu 324 shown in FIG. 5, the routine 400 shown in FIG. 6A begins executing at the "begin" bubble 402. Microprocessor 200 waits for release of the user control switch 106 (block 404), and then controls display 108 to display an "auxiliary control" prompt 406 to alert the user that system 100 is now operating in the "pass through" mode. Routine 400 then enters a loop to detect switch closures of user control switch 106. If the user provides a "red" switch closure, microprocessor 200 writes appropriate data to latch 260 to close the "red" relay-controlled switch 262(13) and to open the "yellow" relay-controlled switches 262(12) (block 410). Similarly, if the user provides a "yellow" type switch closure of user control switch 106, microprocessor 200 writes appropriate data to latch 260 to open the "red" relay-controlled switch 262(13) and to close the "yellow" relay-controlled switches 262(12) (block 412). Similarly, if user control switch 106 is a type of switch that can provide "yellow" and "red" switch closures simultaneously, microprocessor 200 can sense that both of switches 160, 166 are closed and can mimic that switch closure by closing both "red" relay-controlled switch 262(13) and "yellow" relay-controlled switch 262(12) (block 414). Blocks 410, 412, 414 thus control the contacts 266–272 of relays 262(12), 262(13) under microprocessor 200 control in imitation of user control 106.

If microprocessor 200 detects any switch closure ("red," "yellow" or "both"), then the microprocessor begins displaying a prompt "Countdown x sec" on display 108 (and may also if desired provide an audible countdown prompt via speech synthesizer 228) (block 416, FIG. 6B). System 100 may provide a configuration choice to allow the user to program the "time to exit" value. This value should be preferably be set for an interval in excess of the longest expected switch closure for operating the auxiliary device. Microprocessor 200 then initializes a one-second timer (e.g., by setting a "global variable" called "ticks" to 61) (block 418) and updates the display prompt (block 420). Microprocessor then detects whether the user has released the user control switch 106 (decision block 422). If the user has not released the user control switch 106 ("yes" exit to decision block 422), then microprocessor 200 checks whether the telephone circuit 230 indicates an incoming call (decision block 424). If there is no incoming call ("no" exit to decision block 424), then microprocessor 200 detects whether the timer has timed out (e.g., by testing whether "ticks" has been decremented to zero) (decision block 426). If the timer has not timed out ("no" exit to decision block 426), the microprocessor loops back to repeat decision blocks 422, 424. Once the timer does time out ("yes" exit to decision block 426), microprocessor 200 determines whether the total predetermined countdown time has been counted (decision block 428). If not ("no" exit to decision block 428), then microprocessor 200 repeats block 418–1426 to time another one-second interval and to update the display with a decremented time value ("no" exit to decision block 428). If the total programmed countdown time has been timed ("yes" exit to decision block 428), or if at any point during the process the microprocessor detects that the telephone is ringing ("yes" exit to decision block 424), then the microprocessor performs steps to discontinue the "pass through" mode and to instead begin operating again in the "normal" mode.

Referring to FIG. 6C, to cease operating in the "pass through" mode the microprocessor causes a message (e.g., "OK, let go") to be displayed on display 108 and/or uttered by speech synthesizer 22) (block 430), and then waits for release of the user control switch 106 (block 432). Once the user releases the user input control switch 106, microprocessor 200 writes data to latch 260 to open both the relay-controlled switches 262(12), 262(13) in the preferred embodiment (block 434) and then returns main unit 102 to the "normal" mode so that closures of user control switch 106 are no longer mimicked or emulated by jack 190 (block 436). Microprocessor 200 may at this point return to the "additional controls" submenu 324 (or to the "home" menu 302 if desired) (block 436).

The positioning of block 434 after block 432 in the preferred embodiment allows the user to make closures longer than the programmed "time out" period, and also permits the user to continue the auxiliary interface control even after an exit "event" such as telephone ringing occurs. Thus, if the user is actuating user control switch 106 when the telephone rings, system 100 is "courteous" in that it waits for the user to release the user control switch before quickly transferring control to the telephone functions.

Referring back again to FIG. 6A, if microprocessor 200 detects that the user has not actuated the user control switch 106 ("none" exit to block 408), then the microprocessor writes to data latch 260 to cause both of relays 262(12), 262(13) to open (block 438), and then displays a "very long=exit" prompt on display 108 to let the user know how to escape from the "pass through" mode (block 440). Microprocessor 200 then enters an "idle state loop" 442 in which it continually checks for closures of user control switch 106 (decision block 444) and for an incoming telephone call (decision block 446). Occurrence of an incoming telephone call at any time (as detected by decision block 446 and decision block 424) controls microprocessor 200 to immediately discontinue the "pass through" mode so that the user can instantly begin controlling telephone circuits 230 to answer the telephone call. If desired, an exit from routine 400 on this basis may instantly invoke the phone submenu 312 (or a further "answer" sub-submenu if desired) so that the user does not have to go through several additional switch closures to answer the phone. It is very frustrating to miss a telephone call, and severely disabled users may lack sufficient dexterity to rapidly actuate the user control switch 106 several times. To avoid frustration (of user and caller), the preferred embodiment provides this streamlined exit from the "pass through" mode back to a "normal" telephone answering mode so that the user can immediately discontinue operating an external device connected to jack 190 and to instead answer the telephone and perform other associated telephone control functions. This "auto telephone" feature (i.e., decision blocks 446, 424) can be selectively enabled and disabled upon configuring system 100, as not all users might want to immediately escape from the "pass through" mode when the telephone rings.

The preferred embodiment thus provides a pair of isolated single-pole-single-throw relay contacts and also provides the "pass through" mode control of these relay contacts under microprocessor/software control. This arrangement provides an ability to share a momentary "dual" input switch such as a sip and puff, joystick, two-position tongue, etc. between two or more pieces of needed equipment without having to swap wires. The user's existing control switch 106 plugs into the system rear panel 150 jack 106a using a standard stereo plug connection in which "tip" is switch 1, "ring" is switch 2, and "sleeve" is common. Another jack 190 on the rear panel 150 provides the "switch" output relay port. This output jack 190 may also utilize a standard male-male plug extension cable to connect system 100 to an existing, second piece of disability equipment.

When the user stops on the main menu scan for the "auxiliary control interface" selection and sips (or puffs, depending upon the switch wiring), system 100 will enter a "pass through" mode and will not "wake up" until a long closure is made by the user/user switch. During the "pass through" mode of operation, system 100 remains on the "auxiliary interface" menu selection and the microprocessor 200 steers all switch closures of user control switch 106 through drivers and relays which effectively permit the user's switch to simply loop through main unit 102 and feed other disability equipment. For example, sipping and puffing (or other manual control switch actuation) by the user during the "pass through" mode permits the user to now control augmentative communication devices, computer control systems for the disabled and other needed—perhaps existing—equipment that the disabled user deems necessary for their limited independence and work. The aforementioned time to disengage the "pass through" mode may be user settable in a configuration menu.

The preferred embodiment may be modified to enter the "auxiliary control interface" "pass through" mode whenever the user actuates user control switch 106 for more than a predetermined time period. This would allow the user to rapidly access the "pass through" mode without having to go through the "auxiliary control" menu prompt, for example. Thus, the "pass through" mode need not be a "submenu" but could be accessible all the time.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A method of controlling equipment for the disabled comprising:
   (a) electrically detecting user-actuated switch closures;
   (b) selecting, with an electronic processor in response, at least in part, to the detected user-actuated switch closures, between first and second operating modes;
   (c) in the first operating mode, selecting menu options in response to said detected switch closures and automatically controlling at least first equipment based on the selected menu options;
   (d) in the second, "pass through" mode, automatically generating, at least in part in response to said detected user-actuated switch closures, further output switch closures that emulate said user-actuated switch closures;
   (e) controlling at least other equipment with the further output switch closures; and
   (f) remaining in the second mode until a predetermined event occurs.

2. A method as in claim 1 wherein step (f) includes the step of switching from said second mode to said first mode in response to the predetermined event.

3. A method as in claim 2 wherein said event comprises detecting a ringing telephone line.

4. A method as in claim 2 wherein said event comprises detecting a long actuation of said user actuated switch closures.

5. A method as in claim 4 wherein said detecting step comprises timing a programmed time duration.

6. A method as in claim 1 wherein:
   step (b) includes switching from the first mode to the second mode in response, at least in part, to a menu selection based on a user-actuated switch closure, and
   step (f) includes requiring release of said user-actuated switch closure before switching from said second mode to said first mode.

7. A method as in claim 1 wherein said step (c) comprises controlling a pair of electrically isolated switch contacts.

8. Remote control apparatus for controlling disability equipment comprising:
   a microprocessor producing control signals;
   a user-controlled dual action switch connected to said microprocessor; and
   an auxiliary control interface controlled by said microprocessor, said auxiliary control interface providing output switch contact closures in response to microprocessor control signals that selectively emulate closures of said user-controlled dual action switch to control disability equipment.
   wherein the microprocessor selectively operates in a pass through mode to automatically generate control signals controlling the auxiliary control interface to provide output switch control closures that emulate closures of the user-controlled switch, and once operating in the pass through mode the microprocessor remains in the pass through mode until a predetermined event occurs.

9. Apparatus as in claim 8 wherein said microprocessor selectively invokes a normal mode during which closures of said user-actuated switch are not emulated by said auxiliary control interface.

10. Apparatus as in claim 9 wherein said microprocessor changes from said pass through mode to said normal mode upon timing a user actuated switch closure of predetermined duration, the user activated switch closure of predetermined duration comprising the predetermined event.

11. Apparatus for controlling equipment for the disabled comprising:
    detecting means for detecting user-actuated switch closures; and
    electronic control means coupled to said detecting means for:
       (a) in a first mode, selecting from menu options in response to said detected switch closures, at least some of the menu options controlling at least first equipment for the disabled; and
       (b) in a second, "pass through" mode, automatically generating output switch contact closures that emulate said user-actuated switch closures to control at least other equipment for the disabled, and remaining in the pass through mode until a predetermined event occurs.

12. Apparatus as in claim 11 wherein said control means switches from said second mode to said first mode in response to detection of a user activated switch closure of more than a predetermined duration.

13. Apparatus as in claim 11 wherein said control means includes means for detecting a ringing telephone line and for recognizing said predetermined event in response to such detection.

14. Apparatus as in claim 11 wherein said control means includes long actuation detection means for detecting a long actuation of said user actuated switch closures and for recognizing said predetermined event in response to such detection.

15. Apparatus as in claim 14 wherein said long actuation detection means comprises means for timing a user-programmable time duration.

16. Apparatus as in claim 11 wherein said control means includes means for switching from said first mode to said second mode in response, at least in part, to detection of a user-actuated switch closure, and for requiring release of said user-actuated switch closure before switching from said second mode to said first mode.

17. Apparatus as in claim 11 wherein said control means comprises controlling a pair of electrically isolated mechanical switch contacts.

18. Apparatus for controlling equipment for the disabled comprising:
   a circuit that detects user-actuated switch closures; and
   an electronic processing component coupled to the circuit, the electronic processing component:
   (a) selecting between first and second control modes in response, at least in part, to detected user-actuated switch closures;
   (b) in the first mode, selecting menu options in response to said detected switch closures and controlling first equipment for the disabled based on at least some of the selected menu options; and
   (c) in the second, "pass through" mode, generating switch contact closures that emulate said user-actuated switch closures to control other equipment for the disabled, and remaining in the pass through mode until occurrence of a predetermined event.

19. An arrangement for allowing a disabled person to selectively control at least one electrical device, the arrangement comprising:
   a switch that provides switch closures upon actuation by the disabled person;
   an electronic circuit, coupled to said switch, that distinguishes between at least first and second types of closures of said switch actuated by the disabled person the electronic circuit, in use,
   (a) testing for the first and second type of closures, and
   (b) selectively generating outputs to control the at least one electrical device, including (b1) automatically beginning to generate and apply output switching contact closure signals to the electrical device upon said circuit detecting said first type of manually-actuated switch closure, the output switching contact closure signals mimicking said manually-actuated switch closures, (b2) continually testing for the occurrence of a predetermined event, (b3) continuing to apply said mimicked manually-activated output switch closures to the electrical device until the predetermined event occurs, and (b4) thereupon ceasing to apply said mimicked manually-activated output switch closures to the electrical device.

20. An arrangement as in claim 19 wherein said circuit selectively generates control outputs that are responsive to but do not simulate said manually-actuated switch closures in at least one mode of operation.

21. A arrangement as in claim 19 wherein said circuit ceases to selectively generate said control outputs that simulate manually-actuated switch closures upon said circuit detecting said second type of manually-actuated switch closure.

22. A arrangement as in claim 19 wherein said output switch closures provide electrically isolated switch contacts that emulate said manually-actuated switch closures.

23. A method as in claim 5 further including user-programming said programmed duration.

24. An arrangement as in claim 19 wherein said circuit includes means for timing the duration of said closure of said switch.

25. An arrangement as in claim 19 wherein said circuit includes means for testing whether said switch is closed for more than a predetermined duration.

26. An arrangement as in claim 19 wherein said circuit includes means for programming a time duration, and means coupled to said programming means for detecting said first type of closure by testing whether said user closes said switch for longer than said programmed time duration.

27. A method for allowing a disabled person to selectively control at least one electrical device, the method comprising the following steps:
   (a) providing a switch for actuation by the disabled person;
   (b) generating switch closures with the switch upon actuation of the switch by the disabled person;
   (c) testing for a first type of switch closure;
   (d) automatically beginning to generate and apply output switching contact closure signals to the electrical device upon the testing step (c) detecting said first type of manually-actuated switch closure, including the step of causing the output switching contact closure signals to mimic at least some of said person-actuated switch closures;
   (e) continually testing for the occurrence of a predetermined event;
   (f) continuing to apply said mimicked output switch closures to the electrical device until the predetermined event occurs; and
   (g) upon occurrence of the predetermined event, ceasing to apply said mimicked output switch closures to the electrical device.

28. A method as in claim 27 wherein the testing step (e) comprises the step of testing for a second type of switch closure different from the first type of switch closure.

29. A method as in claim 27 wherein the testing step (e) comprises the step of testing whether a predetermined time period has elapsed.

30. A method as in claim 27 wherein step (g) includes the step of automatically routing the output closures to a further electrical device different from the first-mentioned electrical device.

31. A method as in claim 27 wherein step (g) includes the step of beginning to automatically control a menu-driven environmental control operation in response to the switch closures actuated by the disabled person.

* * * * *